United States Patent [19]

Richter

[11] Patent Number: 5,782,905
[45] Date of Patent: Jul. 21, 1998

[54] ENDOVASCULAR DEVICE FOR PROTECTION OF ANEURYSM

[75] Inventor: Jacob Richter, Hasharon, Israel

[73] Assignee: Zuli Holdings Ltd., Ramat Hasharon, Israel

[21] Appl. No.: 643,247

[22] Filed: May 3, 1996

[51] Int. Cl.[6] .................................................. A61F 2/06
[52] U.S. Cl. .................................................. 623/1; 623/12
[58] Field of Search .................................. 623/1, 11, 12; 606/194, 195, 198, 151, 152, 153, 154, 155, 156, 157, 158

[56] References Cited

U.S. PATENT DOCUMENTS

| | | | |
|---|---|---|---|
| 4,601,718 | 7/1986 | Possis et al. | 623/1 |
| 5,507,767 | 4/1996 | Maeda et al. | 623/1 |
| 5,512,291 | 4/1996 | Li | 623/1 |
| 5,551,954 | 9/1996 | Buscemi et al. | 623/1 |

*Primary Examiner*—Debra S. Brittingham
*Attorney, Agent, or Firm*—Kenyon & Kenyon

[57] ABSTRACT

A prosthesis for imparting structural integrity to a blood vessel having an aneurysm comprising a longitudinal member having an external surface, a first end, a second end, and an internal surface defining a longitudinal bore. The internal surface is provided with a constriction to increase the velocity of a fluid passing through the longitudinal bore. A plurality of apertures provide fluid communication between the external surface and the longitudinal bore at the constriction to cause a suction that will diminish the pressure within the aneurysmal sack.

3 Claims, 3 Drawing Sheets

ENDOVASCULAR DEVICE FOR PROTECTION OF ANEURYSM

FIELD AND BACKGROUND OF THE INVENTION

The present invention relates to devices which are implanted within a bodily conduit of a living animal or a human to impart structural integrity. In particular, the present invention is related to intravascular devices for delivery through or implantation in a blood vessel having an aneurysm without many of the disadvantages and dangerous features of known devices.

Aneurysm is a phenomenon in which the wall of a blood vessel, typically an artery, is abnormally dilated due to weakening of the vessel wall. This poses a danger because the blood pressure within the vessel could cause the vessel to rupture.

One conventional approach to treating aneurysms is to utilize intravascular prostheses. Intravascular stents having a constricted diameter for delivery through a blood vessel and an expanded diameter for applying a radially outwardly extending force for treating the aneurysm in a blood vessel are known in the art. These stents are usually covered with a covering, e.g., Teflon or Dacron and serve to substitute for the aneurysmal wall of the blood vessel and relieve pressure on the aneurysmal wall by isolating the aneurysm from the flow of blood within the vessel. One shortcoming of these prior art devices is that poor apposition of the prosthesis to the walls of the vessel being treated may allow blood to flow between the prosthesis and the aneurysm. This blood may create pressure on the aneurysmal wall in an amount sufficient to rupture the vessel at the weakened point of the aneurysm. One conventional approach for dealing with this problem is to insert a stent-like insert in the two ends of the prosthesis in an attempt to push the prosthesis against the wall of the vessel so as to create a tighter seal between the prosthesis and the wall of the vessel being treated. One shortcoming of this approach is that the introduction of the stents requires that additional pressure be applied to the area being treated with the possibility that the pressure could cause damage to the vessel being treated. Another shortcoming of this approach is that in this procedure blood may leak into the aneurysmal sack.

Therefore, it would be highly desirable to have a prosthesis for imparting structural integrity to a blood vessel having an aneurysm that minimizes the risk that there will be blood pressure in the aneurysmal sack.

OBJECTS AND SUMMARY OF THE INVENTION

It is an object of this invention to provide a prosthesis for imparting structural integrity to a blood vessel having an aneurysm that minimizes the risk that blood will leak into the aneurysmal sack and sustain pressure on it.

It is another object of this invention to provide a one piece prosthesis for imparting structural integrity to a blood vessel having an aneurysm that minimizes the risk that blood will leak into the aneurysmal sack and sustain pressure on it.

It is still another object of this invention to provide a prosthesis for imparting structural integrity to a blood vessel having an aneurysm, comprising: a) a longitudinal member having an external surface, a first end, a second end, and an internal surface defining a longitudinal bore, said internal surface provided with means for increasing the velocity of a fluid passing through said longitudinal bore; and b) a plurality of apertures in fluid communication with said external surface and said longitudinal bore.

DETAILED DESCRIPTION OF THE INVENTION

Figure 1:
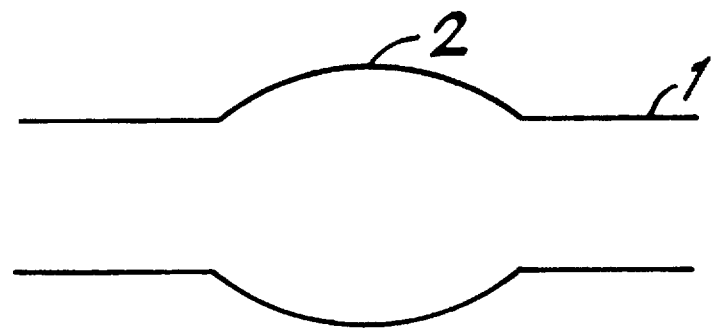
FIG. 1 shows a longitudinal side view of a blood vessel with an aneurysm.
Figure 2:
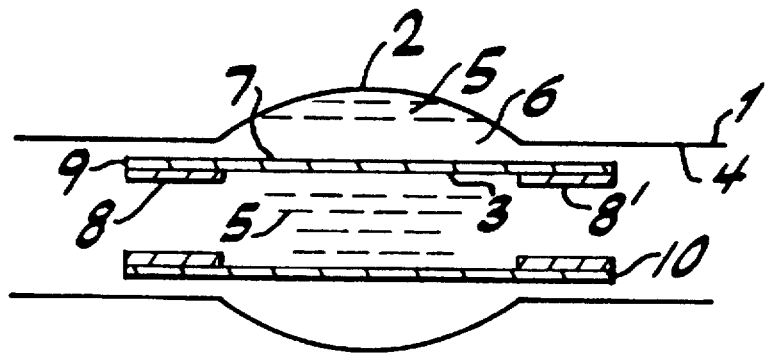
FIG. 2 shows a longitudinal side view of a conventional prosthesis with stents applied to its two ends applied to the blood vessel shown in FIG. 1.

FIG. 1 shows a blood vessel 1 with an aneurysm 2. FIG. 2 shows a conventional prosthesis 3 disposed at the site of the aneurysm 2. Sub-optimal apposition of prosthesis 3 to the internal wall 4 of the blood vessel 1 allows blood 5 to leak or seep into the aneurysmal sack ("AS") 6 which is the space 6 between the aneurysm 2 and the external wall 7 of the prosthesis 3.

FIG. 2 also shows a conventional procedure for increasing the seal between the external surface 7 of the conventional prosthesis 3 and the external wall 4 of the blood vessel 1. After the prosthesis 3 has been placed at the site of the aneurysm 2, stent-like inserts 8 and 8' are inserted at the ends 9 and 10 of the conventional prosthesis 3. The stents 8 and 8' apply pressure to the ends 9 and 10 forcing them into closer contact with the internal wall 4 of the blood vessel 1. One shortcoming of this procedure is that the pressure required could result in damage to the blood vessel 1. Another shortcoming is that the possibility remains that blood 5 could still leak into the aneurysmal sack 6 because of an inadequate seal between the external wall 7 of the prosthesis 3 and the aneurysm 2.

Figure 3:
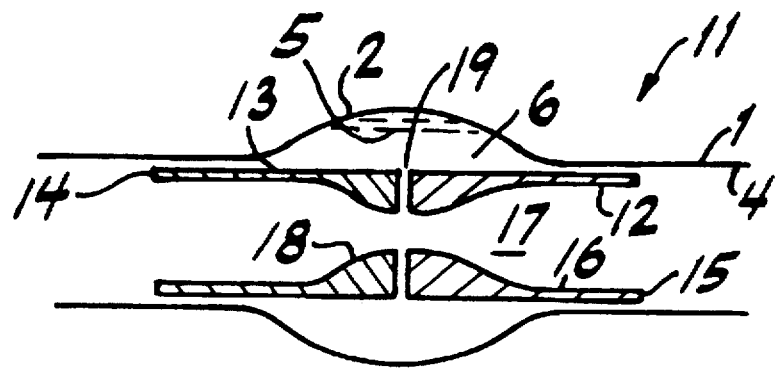
FIG. 3 shows a longitudinal side view of a prosthesis constructed in accordance with the invention applied to the blood vessel of FIG. 1.
Figure 4:
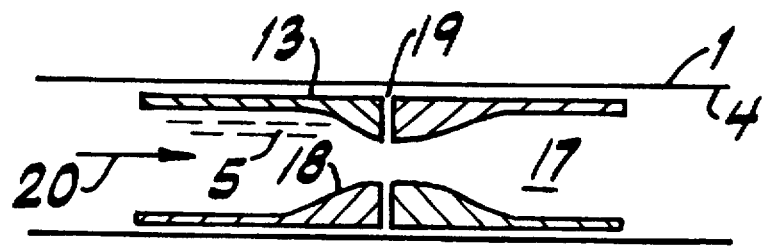
FIG. 4 shows a longitudinal side view of a prosthesis constructed in accordance with the invention applied to the blood vessel of FIG. 1 after the aneurysmal sack has been sucked into contact with the prosthesis.
Figure 5:
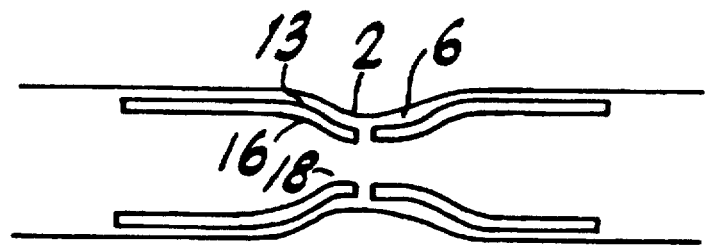
FIG. 5 shows an alternative embodiment of a prosthesis constructed in accordance with the invention applied to the blood vessel of FIG. 1 after the aneurysmal sack has been sucked into contact with the prosthesis.

FIG. 3 shows a prosthesis 11 constructed in accordance with this invention disposed in a blood vessel 1. The prosthesis 11 comprises a longitudinal member 12 having an external surface 13, an internal surface 16, a first end 14, and a second end 15. The internal surface 16 defines a longitudinal bore 17. The internal surface 16 is provided with a means 18 for increasing the velocity of blood 5 flowing through said longitudinal bore 17. In a preferred embodiment this means 18 is a smoothly tapered constriction as shown in FIGS. 3, 4 and 5. If the velocity of a moving fluid increases for any reason, the static pressure of the fluid drops. This reduction of static pressure with increasing velocity is known as the Venturi effect. The effect can be very simply demonstrated. If two sheets of paper are held parallel to each other and the velocity of the air layer between them is increased, for example by blowing, the two sheets are seen to move towards each other. This is because the static pressure between the two sheets is decreased as compared to the surrounding atmospheric pressure. As shown in FIGS. 3, 4 and 5, the internal surface of the apparatus of this invention is provided with a smoothly tapered constriction or throat 18. The presence of this constriction causes the velocity of the blood 5 to increase which is accompanied by a fall in static pressure. The structure is similar to a hydrofoil, i.e., the shape of the cross-section of a hydroplane, which has a greater curvature on a first major surface than on a second major surface. When a fluid, such as water, moves relative to such an object the rate of flow is greater over the surface of greatest curvature. The resulting pressure difference between the greater curved surface and lesser curved surface gives rise to suction. A plurality of apertures 19 are in fluid communication with the external surface 13 and the longitudinal bore 17 to allow blood 5 to flow from the aneurysmal sack 6 into the longitudinal bore 17.

FIG. 4 shows that as blood 5 flows in the direction of the arrow 20, blood 5 that may have collected in the aneurysmal sack 6 is drawn or sucked into the longitudinal bore 17 through apertures 19. The internal wall 4 of the blood vessel 1 is drawn towards the external surface 13 of the prosthesis 11 due to the decreased static pressure within the longitudinal bore 17 which results from the increase in the velocity of the moving blood 5 caused by the constriction 18. Thus, the internal pressure on the aneurysmal sack 6 is diminished.

FIG. 5 shows an alternative embodiment of the invention wherein the external surface 13 is parallel to the internal surface 16

What is claimed is:

1. A prosthesis for imparting structural integrity to a blood vessel having an aneurysm defining an aneurysmal sack, comprising:
   a) a longitudinal member having an external surface, a first end, a second end, and an internal surface defining a longitudinal bore to permit passage of a moving fluid having a velocity, said internal surface provided with means for increasing the velocity of a fluid passing through said longitudinal bore; and
   b) a plurality of apertures in fluid communication with said external surface and said longitudinal bore, said apertures sized and disposed to permit blood to be drawn from said aneurysmal sack into said longitudinal bore.

2. The apparatus of claim 1, wherein said means is a smoothly tapered constriction.

3. The stent of claim 2, wherein said external surface defines a substantially uniform external diameter of said longitudinal member.

* * * * *

UNITED STATES PATENT AND TRADEMARK OFFICE
CERTIFICATE OF CORRECTION

PATENT NO.   : 5,782,905
DATED        : July 21, 1998
INVENTOR(S)  : Jacob Richter It is certified that error appears in the above-identified patent and that said Letters Patent is hereby corrected as shown below:

Column 4,
Line 17, change "apparatus" to -- prosthesis --.
Line 19, change "stent" to -- prosthesis --.

Signed and Sealed this

Tenth Day of December, 2002

JAMES E. ROGAN
*Director of the United States Patent and Trademark Office*